United States Patent
Greenberg et al.

(10) Patent No.: US 10,786,670 B2
(45) Date of Patent: **\*Sep. 29, 2020**

(54) VISUAL PROSTHESIS INCLUDING AN IMPROVED VIDEO PROCESSING UNIT

(71) Applicant: Second Sight Medical Products, Inc., Sylmar, CA (US)

(72) Inventors: Robert J Greenberg, Los Angeles, CA (US); Arup Roy, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 15/967,393

(22) Filed: Apr. 30, 2018

(65) Prior Publication Data
US 2018/0243561 A1 Aug. 30, 2018

Related U.S. Application Data

(62) Division of application No. 15/156,090, filed on May 16, 2016, now Pat. No. 9,974,954.

(60) Provisional application No. 62/161,736, filed on May 14, 2015.

(51) Int. Cl.
*A61N 1/36* (2006.01)
*A61N 1/372* (2006.01)
*A61N 1/05* (2006.01)

(52) U.S. Cl.
CPC ........ *A61N 1/36046* (2013.01); *A61N 1/0543* (2013.01); *A61N 1/37247* (2013.01)

(58) Field of Classification Search
None
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,974,699 B2 | 7/2011 | Tano et al. | |
| 9,044,591 B2 | 6/2015 | Greenberg et al. | |
| 9,108,056 B2 | 8/2015 | McClure et al. | |
| 9,172,345 B2 * | 10/2015 | Kok | H03G 3/32 |
| 9,298,324 B1 * | 3/2016 | Rowe | G06F 3/044 |
| 9,314,626 B2 * | 4/2016 | McDermott | A61N 1/36046 |
| 9,526,895 B2 | 12/2016 | McClure et al. | |
| 2008/0077196 A1 * | 3/2008 | Greenberg | A61N 1/0543 607/54 |

\* cited by examiner

*Primary Examiner* — Brian T Gedeon
(74) *Attorney, Agent, or Firm* — Scott B. Dunbar

(57) ABSTRACT

The present invention is an improved visual prosthesis including a video processing unit with user controls optimized for use by blind individuals. The controls include easily identifiable shapes. The controls are programmable to provide improved usability with a simple tactile interface.

11 Claims, 8 Drawing Sheets

VISUAL PROSTHESIS INCLUDING AN IMPROVED VIDEO PROCESSING UNIT

CROSS REFERENCE TO RELATED APPLICATIONS

This patent application is a divisional application of U.S. patent application Ser. No. 15/156,090, filed May 16, 2016, for Visual Prosthesis including an Improved Video Processing Unit, which incorporates by reference and claims priority to U.S. Provisional Application 62/161,736, filed May 14, 2015, for Video Processing Unit for a Visual Prosthesis. This patent application is related to and incorporates by reference U.S. Pat. No. 8,798,756 for Video Processing Unit for a Visual Prosthetic Apparatus. The present invention represents a next generation improvement over the devices described in U.S. Pat. No. 8,798,756. The users controls described here are intended to work with a visual prosthesis system as described in U.S. Pat. No. 8,798,756.

FIELD OF THE INVENTION

The present disclosure is directed to a video processing unit for a visual prosthesis, and more specifically to improved user controls for a visual prosthesis.

SUMMARY OF THE INVENTION

The present invention is an improved visual prosthesis including a video processing unit with user controls optimized for use by blind individuals. The controls include easily identifiable shapes. The controls are programmable to provide improved usability with a simple tactile interface. A programmable slider serves a variety of input functions.

DETAILED DESCRIPTION OF THE PREFERRED EMBODIMENT

Figure 1:
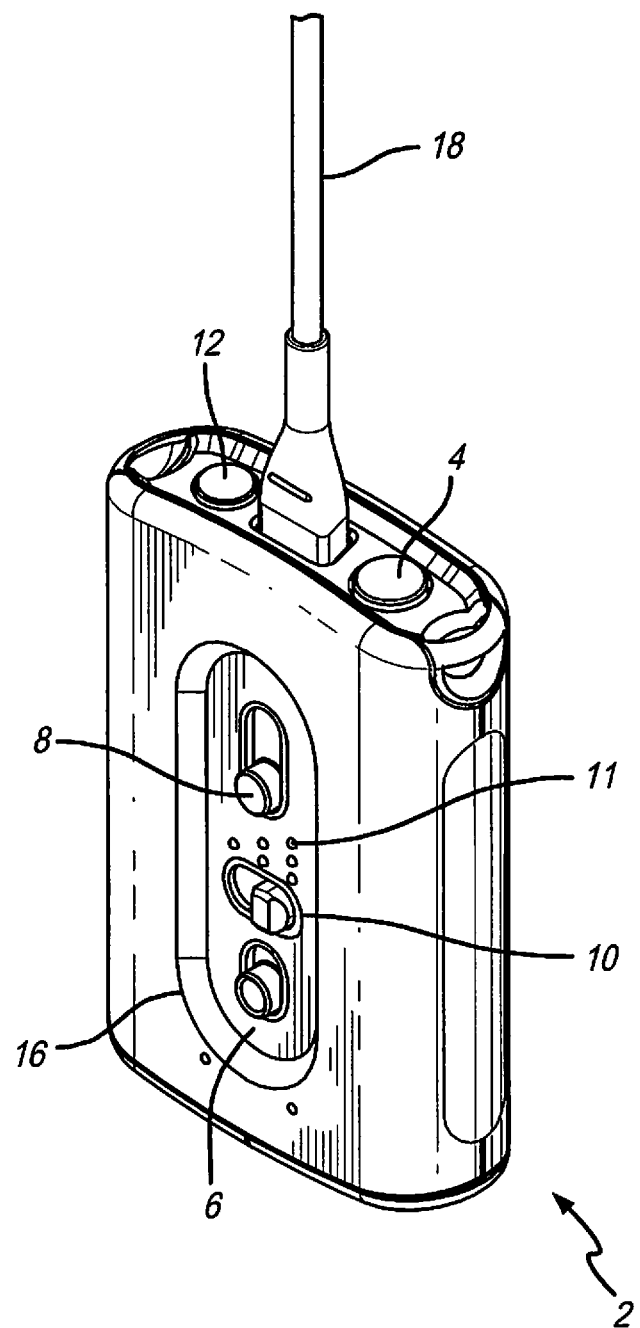
FIG. 1 is a top right perspective view of the video processing unit.
Figure 2:
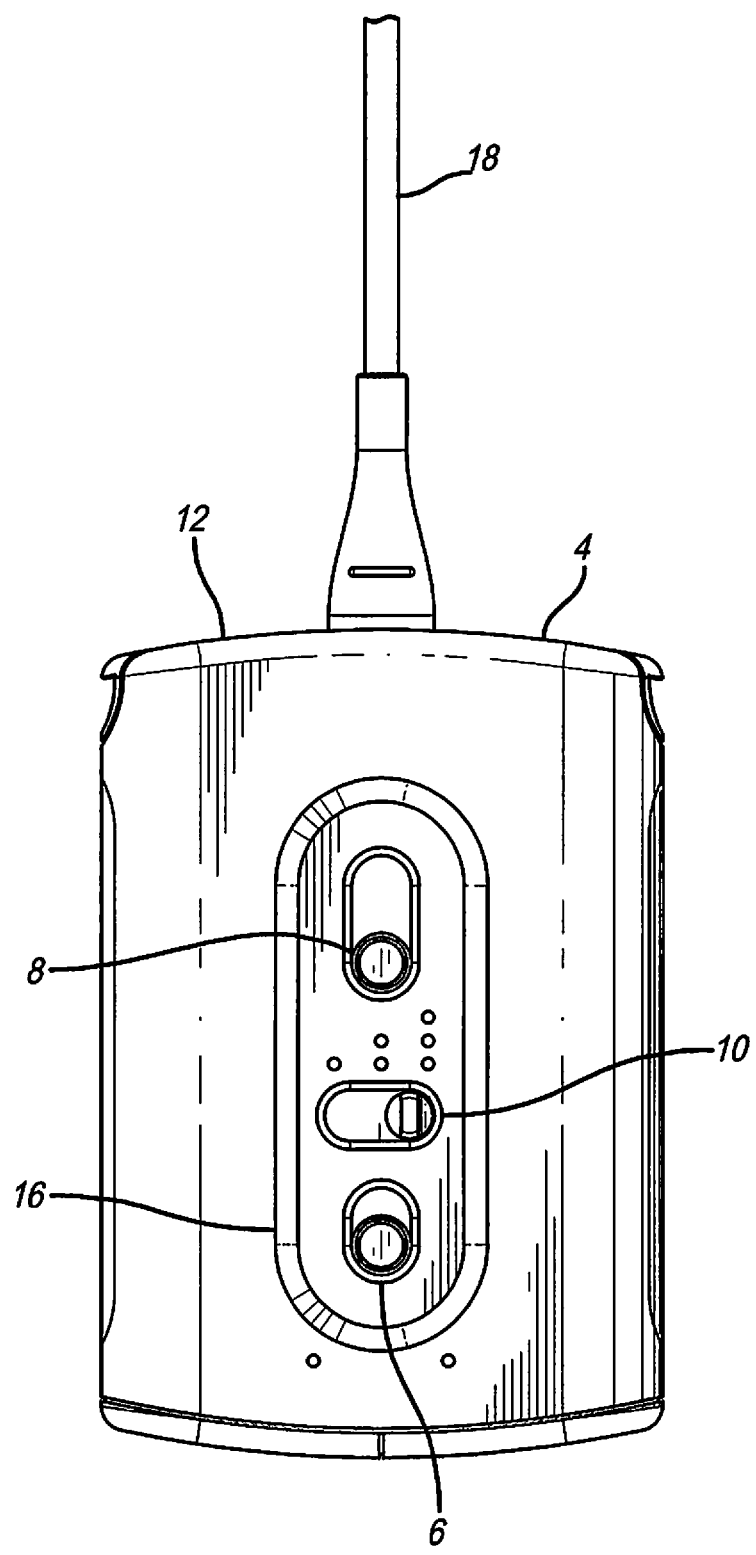
FIG. 2 is a front view of the video processing unit.
Figure 3:
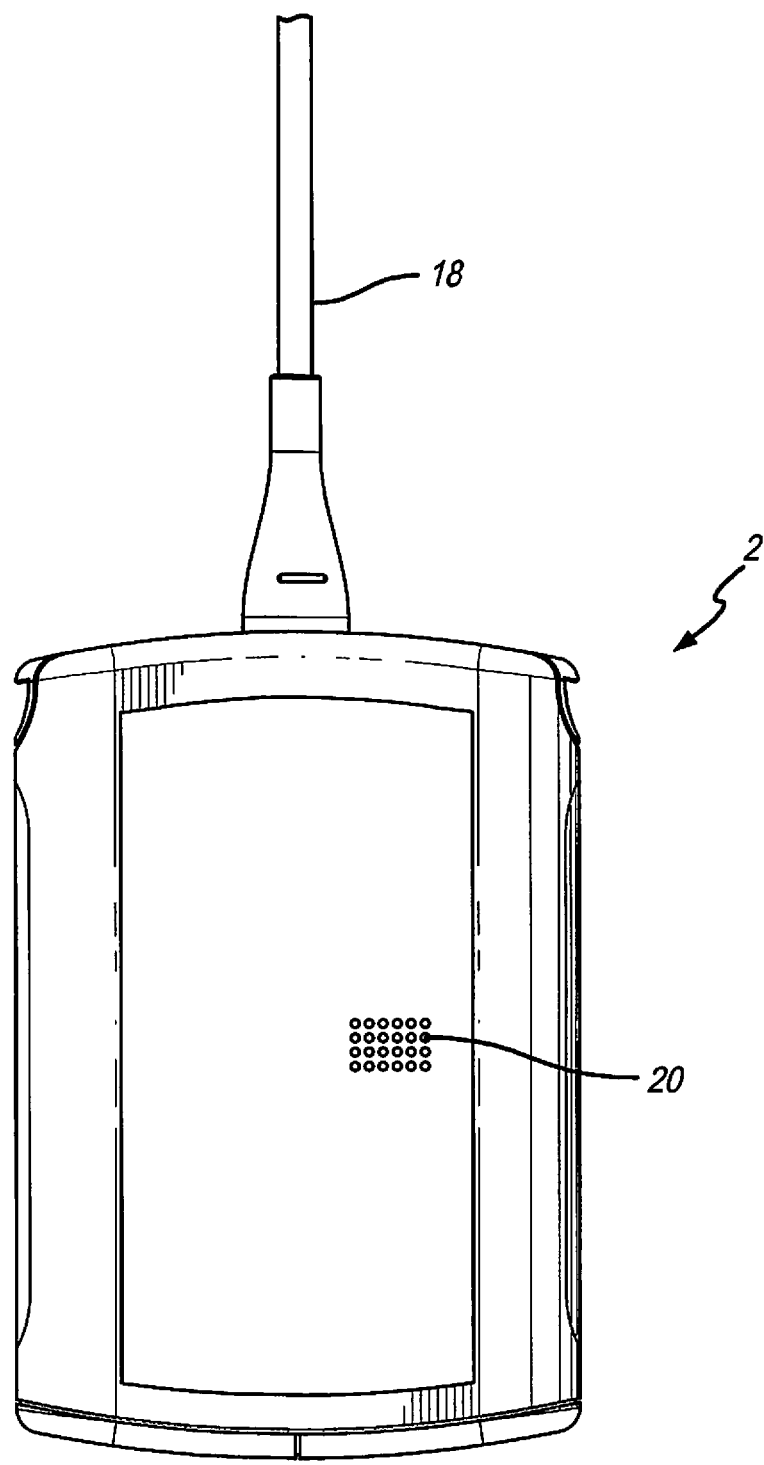
FIG. 3 is a rear view of the video processing unit.
Figure 4:
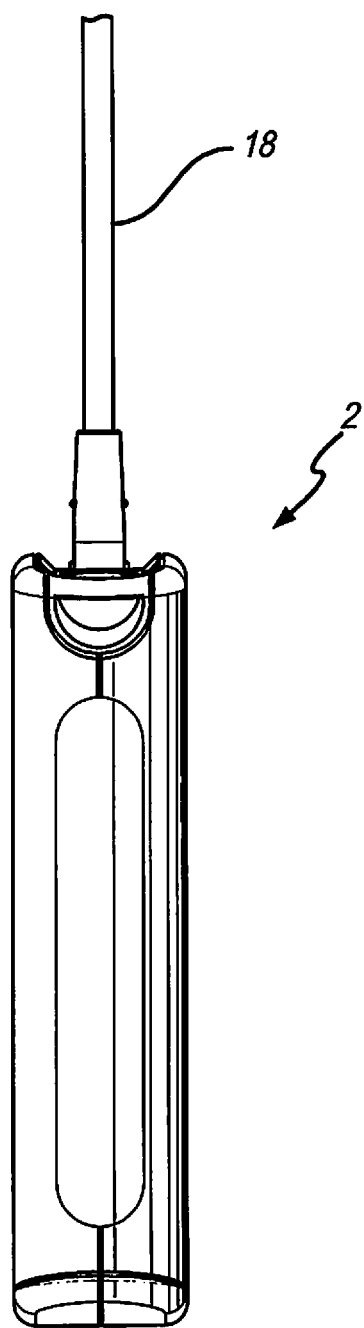
FIG. 4 is a right side view of the video processing unit.
Figure 5:
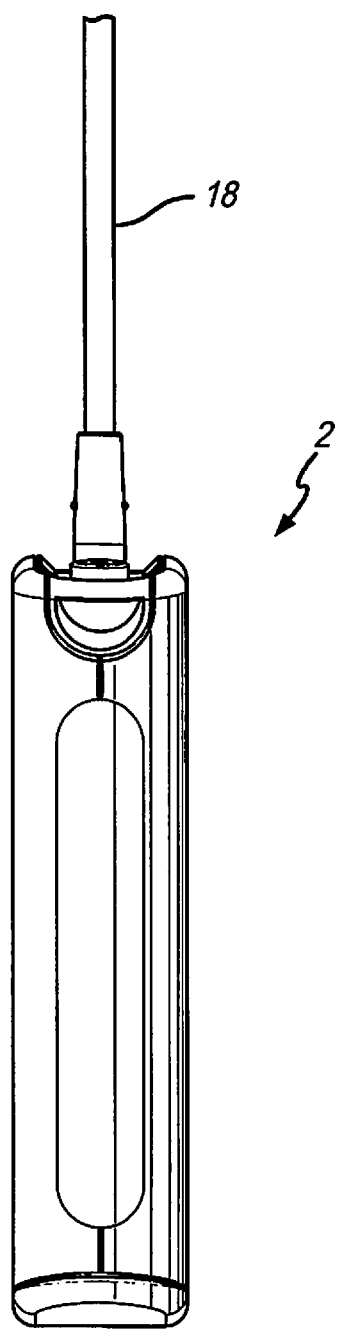
FIG. 5 is a left side view of the video processing unit.
Figure 6:
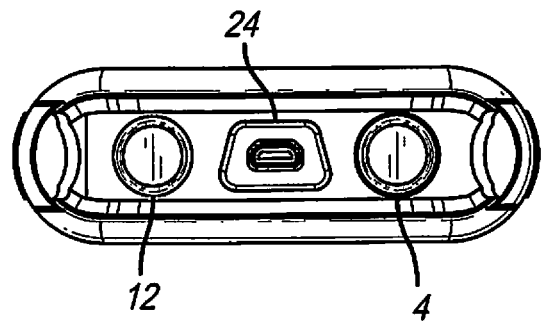
FIG. 6 is a top view of the video processing unit.
Figure 7:
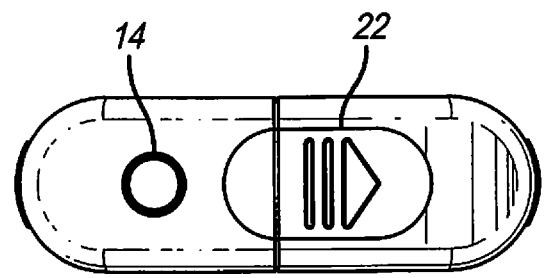
FIG. 7 is a bottom view of the video processing unit.

Referring to FIGS. 1-7, user input controls on the housing of the video processing unit 2 include a power button 4 and a mute button 12 on the top of video processing unit 2 housing. The power button 4 is depressed for a predetermined time, about a second, to turn the video processor 2 on or off. The mute 12 button mutes audio feedback. On the face of the video processing unit 2 housing is an analog slider 8. In the default mode, the analog slider 8 controls brightness. The analog slider 8 is a potentiostat that returns its value to the microprocessor in the video processing unit 2 through an analog to digital converter. It can be programmed for any function. Alternate functions can include gain, sensitivity (including separate indoor and outdoor settings), exposure, contrast or zoom (zoom in, zoom out, and 1-1), total brightness limit (useful for photo phobic patients) and frequency of stimulation.

Below the analog slider 8 is a three position selector switch 10 to choose between programmable options. The three position selector switch 10 includes tactile marks 11 to aid blind users. The three position selector switch 10 is also programmable for function. The position selector switch 10 can select between predefined filters or alter the function of the analog slider 8 as discussed above. Below the three position selector switch 10 is an invert switch 6. The invert switch 6 inverts the image; light is dark and dark is light. All of the buttons are programmable to multiple functions. As an example, the power button 4 and the mute button 12 can be programmed as yes and no responses to menu functions. An additional programmable button 14 is on the bottom of the housing. The battery cover 22 is also on the bottom of the housing and includes tactile markings to aid the blind user.

The buttons are arranged to maximize use by blind users. An inset 16 surrounds the analog slider 8, three position selector 10 and invert switch 6. This allows a user to quickly identify the front and back of the video processing unit 2 housing and to find the location of user controls. Top and bottom orientation is achieved by the location of the data cable 18 in the top. The data cable 18 is connected to the top via the data cable connector 24. The video processing unit 2 further includes a speaker 20 on the back side opposite the user controls. The speaker 20 can be used for informative signals like those associated with turning on or off, error warning or announcements supporting use of the menu system.

Figure 8:
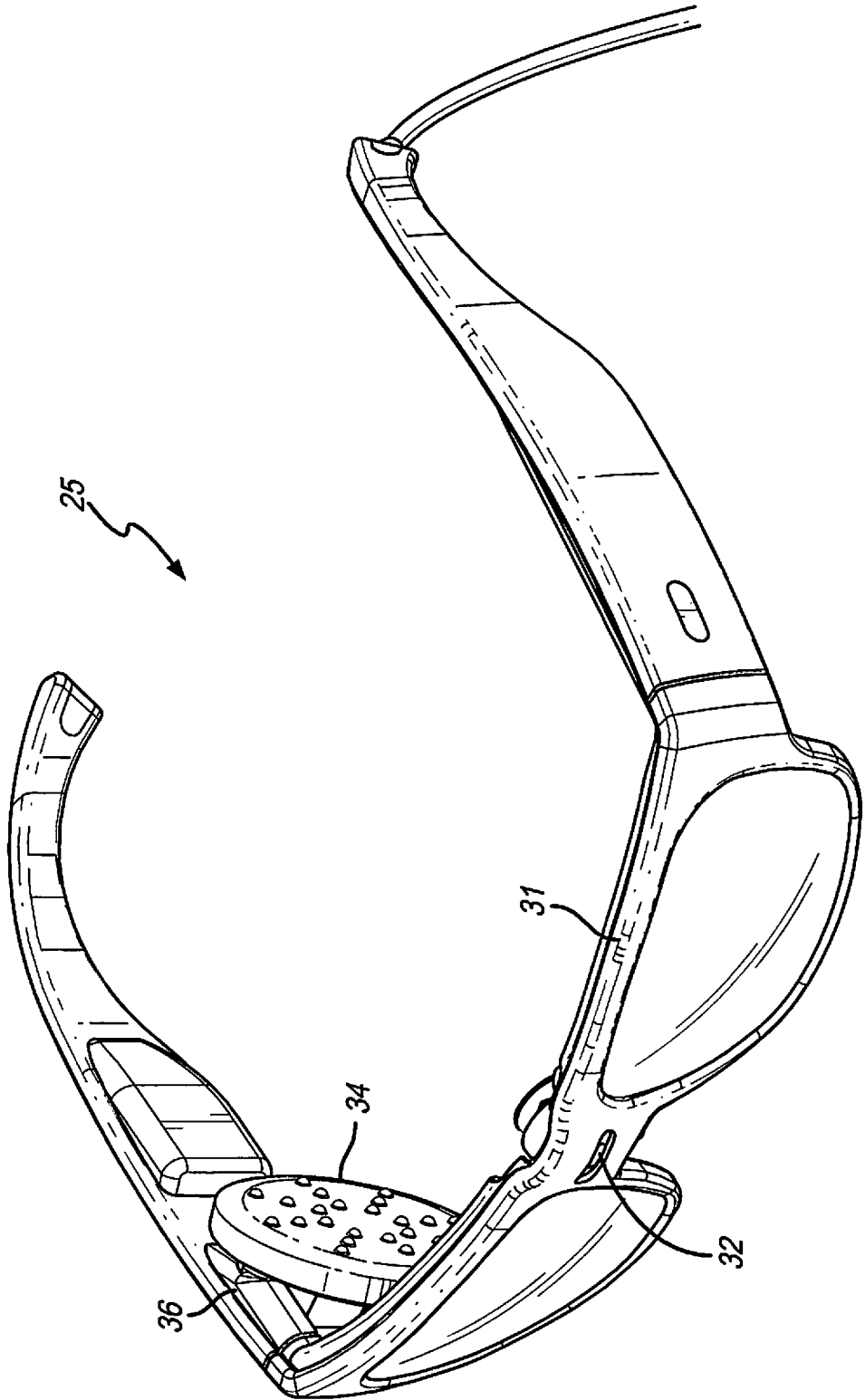
FIG. 8 is a perspective view of the glasses.

Referring to FIG. 8, the glasses 25 may comprise, for example, a frame 31 holding a camera 32, an external coil 34 and a mounting system 36 for the external coil 34. The mounting system 36 may also enclose the RF circuitry. In this configuration, the video camera 32 captures live video. The video signal is sent to the Video Processing Unit 2 (shown in FIGS. 1-7), which processes the video signal and subsequently transforms the processed video signal into electrical stimulation patterns or data. The electrical stimulation data are then sent to the external coil 34 that sends both data and power via radio-frequency (RF) telemetry to the coil 116 of the retinal stimulation system 100, shown in FIG. 9. The coil 116 receives the RF commands which control the application specific integrated circuit (ASIC) inside the electronics package 114, which in turn delivers stimulation to the retina of the subject via a thin film electrode array (TFEA) 112. In one aspect of an embodiment, light amplitude is recorded by the camera 32. The VPU 2 may use a logarithmic encoding scheme to convert the incoming light amplitudes into the electrical stimulation patterns or data. These electrical stimulation patterns or data may then be passed on to the Retinal Stimulation System 100, which results in the retinal cells being stimulated via the electrodes in the electrode array 110 (shown in FIG. 9). In one exemplary embodiment, the electrical stimulation patterns or data being transmitted by the external coil 34 is binary data. The external coil 34 may contain a receiver and transmitter antennae and a radio-frequency (RF) electronics card for communicating with the internal coil 116.

Figure 9:
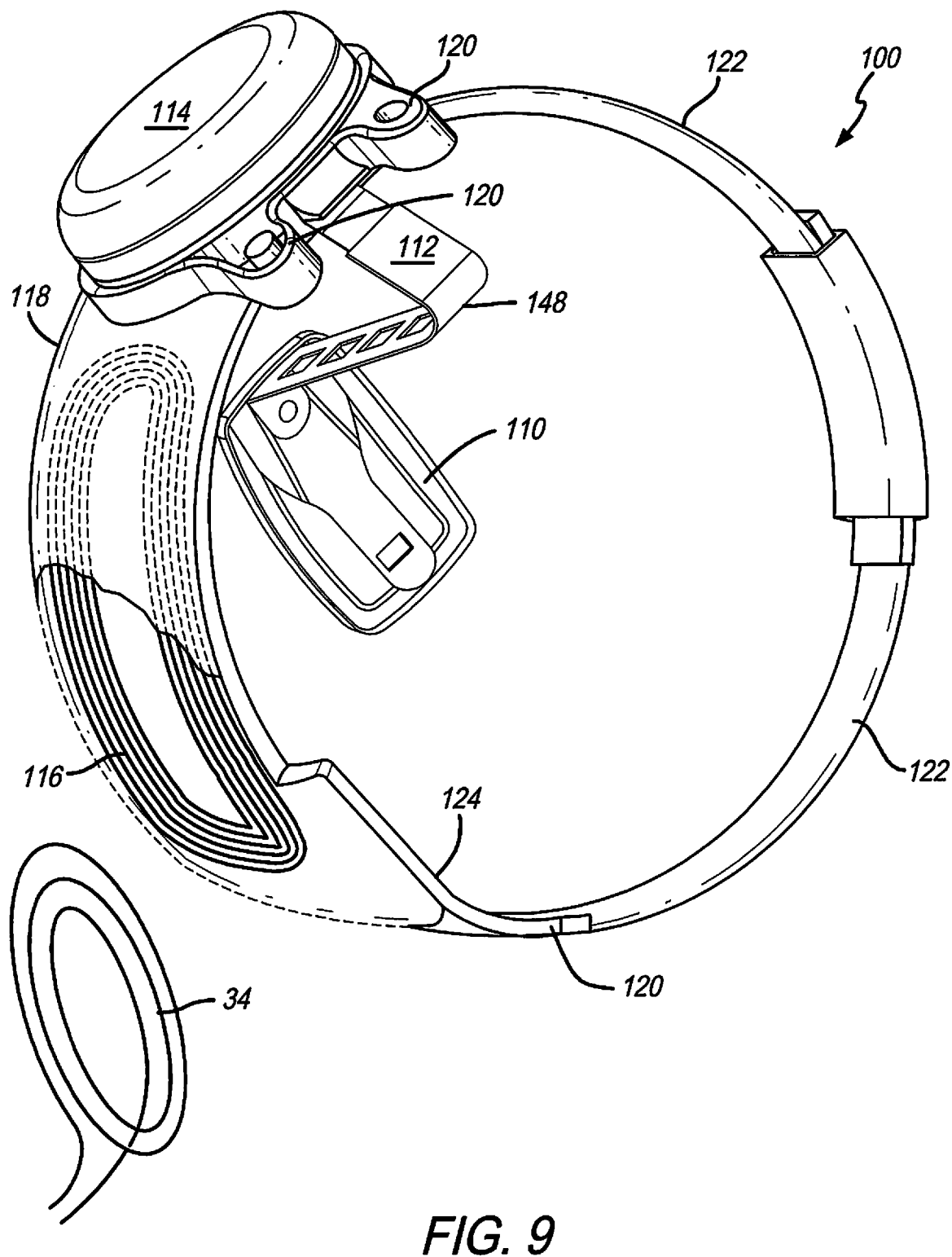
FIG. 9 is a perspective view of the implanted portion of the visual prosthesis.

FIG. 9 shows a perspective view of the implanted portion of the preferred visual prosthesis. A flexible circuit 112 includes a flexible circuit electrode array 110 which is mounted by a retinal tack (not shown) or similar means to the epiretinal surface. The flexible circuit electrode array 110 is electrically coupled by a flexible circuit cable 112, which pierces the sclera and is electrically coupled to an electronics package 114, external to the sclera.

The electronics package 114 is electrically coupled to a secondary inductive coil 116. Preferably the secondary inductive coil 116 is made from wound wire. Alternatively, the secondary inductive coil 116 may be made from a flexible circuit polymer sandwich with wire traces deposited between layers of flexible circuit polymer. The secondary inductive coil receives power and data from a primary inductive coil 34, which is external to the body. The electronics package 114 and secondary inductive coil 116 are held together by the molded body 118. The molded body 118 holds the electronics package 114 and secondary inductive coil 116 end to end. The molded body 118 holds the secondary inductive coil 116 and electronics package 114 in the end to end orientation and minimizes the thickness or height above the sclera of the entire device. The molded body 118 may also include suture tabs 120. The molded body 118 narrows to form a strap 122 which surrounds the sclera and holds the molded body 118, secondary inductive coil 116, and electronics package 114 in place. The molded body 118, suture tabs 120 and strap 122 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 116 and molded body 118 are preferably oval shaped. A strap 122 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

The molded body 118 narrows into a fan tail 124 at the strap 122. When implanting the visual prosthesis, it is necessary to pass the strap 122 under the eye muscles to surround the sclera. The secondary inductive coil 116 and molded body 118 must also follow the strap 122 under the lateral rectus muscle on the side of the sclera. The implanted portion of the visual prosthesis is very delicate. It is easy to tear the molded body 118 or break wires in the secondary inductive coil 116. In order to allow the molded body 118 to slide smoothly under the lateral rectus muscle, the molded body 118 is shaped in the form of a fan tail 124 on the end opposite the electronics package 114.

Accordingly, what has been shown is an improved visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A visual prosthesis comprising:
   a camera receiving a video image and sending a video signal;
   a video processing unit, receiving the video signal and converting the video signal to stimulation patterns including
      a processor circuit altering the video signal according to user input,
      a housing enclosing the circuit,
      an indented portion in the housing configured to be identified by touch,
      a programmable slider within the indented portion for providing user input, the programmable slider programmable to control brightness;
   a transmitter receiving stimulation patterns from the video processing unit and sending the wireless signals; and
   an implantable portion receiving the wireless signals and suitable to stimulate visual neurons.

2. The visual prosthesis according to claim 1, wherein the indented portion includes a beveled indentation.

3. The visual prosthesis according to claim 1, wherein the indented portion is oval in shape.

4. The visual prosthesis according to claim 1, wherein the housing includes tactile features in assist a blind person in orienting the housing and locate the user controls.

5. The visual prosthesis according to claim 1, wherein the programmable slider is a variable resistor with an output connected to an analog digital converter.

6. The visual prosthesis according to claim 1, wherein the programmable slider is a potentiostat.

7. The visual prosthesis according to claim 1, wherein the programmable slider is programmable to control gain.

8. The visual prosthesis according to claim 1, wherein the programmable slider is programmable to control sensitivity.

9. The visual prosthesis according to claim 1, wherein the programmable slider is programmable to control exposure.

10. The visual prosthesis according to claim 1, wherein the programmable slider is programmable to control contrast.

11. The visual prosthesis according to claim 1, wherein the programmable slider is programmable to control zoom.

* * * * *